United States Patent
Tirkel et al.

(10) Patent No.: US 6,313,643 B1
(45) Date of Patent: Nov. 6, 2001

(54) TERMITE DETECTION SYSTEM

(75) Inventors: Anatol Zygmunt Tirkel, East Brighton; Gregory John Sanderson, Via Toowoomba; Robert James Davies, Kawungan, all of (AU)

(73) Assignee: J.I. Peston Pty. Ltd., Archerfield (AU)

( * ) Notice: Subject to any disclaimer, the term of this patent is extended or adjusted under 35 U.S.C. 154(b) by 0 days.

(21) Appl. No.: 09/029,960
(22) PCT Filed: Sep. 4, 1996
(86) PCT No.: PCT/AU96/00548
 § 371 Date: Jun. 2, 1998
 § 102(e) Date: Jun. 2, 1998
(87) PCT Pub. No.: WO97/09611
 PCT Pub. Date: Mar. 13, 1997

(30) Foreign Application Priority Data

Sep. 6, 1995 (AU) .................................................. PN5246
Jan. 31, 1996 (AU) .................................................. PN7807

(51) Int. Cl.[7] .............................. G01S 13/58; G01R 27/04
(52) U.S. Cl. ............................... 324/642; 342/28; 342/27; 119/721
(58) Field of Search .................................. 119/721; 449/6; 342/27, 28; 324/639, 642, 632; 702/40, 189, 190; 706/14, 15, 24

(56) References Cited

U.S. PATENT DOCUMENTS

| | | | |
|---|---|---|---|
| 3,754,254 | * | 8/1973 | Jinman .................................. 342/28 |
| 3,885,234 | | 5/1975 | Fujimoto . |
| 3,890,615 | * | 6/1975 | Moran .................................... 342/28 |
| 4,941,356 | | 7/1990 | Pallaske . |
| 5,214,435 | | 5/1993 | Lopez . |
| 5,285,688 | | 2/1994 | Robbins et al. . |
| 5,519,400 | * | 5/1996 | McEwan ................................ 342/28 |
| 5,521,600 | * | 5/1996 | McEwan ................................ 342/28 |

* cited by examiner

Primary Examiner—Safet Metjahic
Assistant Examiner—Anjan K Deb
(74) Attorney, Agent, or Firm—Christie, Parker & Hale, LLP

(57) ABSTRACT

A method and apparatus of detecting termites in which microwaves are transmitted into a region and reflected microwaves are detected. The received signals are processed to identify the presence or otherwise of termites or other insects. Various hardware configurations and signal processing algorithms are described including planar antenna arrays and neural net signal processing. The system comprises a microwave assembly, modulator and a processor. Microwaves are transmitted into a structure and the reflected microwaves are received in the microwave assembly. The output of the processor is displayed on a display.

45 Claims, 10 Drawing Sheets

TO IF MUX OF ADDER

TERMITE DETECTION SYSTEM

FIELD OF THE INVENTION

THIS INVENTION relates to pest detection by transmitting a microwave signal into a part of a building or other structure for example a wall, floor or ceiling and processing reflections or modulations of the microwave signal to provide a signal indicative of the presence of a pest.

BACKGROUND TO THE INVENTION

Timber eating termites cause damage to property such as buildings. There are numerous ways of killing such pests, however, it is not always easy to detect their presence. As a result, a building structure can be severely damaged by these pests before they are detected. The invention is directed to detecting pests such as termites or other insects, preferably before they cause appreciable damage.

The problem of detecting termites has been addressed in the past but without success. Reference may be had to U. S. Pat. No. 5,285,668 in the name of Robbins and Mueller that describes a system for detecting wood-destroying insects by sensing acoustic emissions generated by the insects as they feed. The major shortcoming of this approach is that termites are not always feeding. The inventors have found that termites may use extensive galleries to move between a feeding region and a nest. The system disclosed in U.S. Pat. No. 5,285,668 will not detect the termites in the galleries. Furthermore, acoustic techniques are prone to spurious signals due to ambient noise.

It is known to use microwaves to kill termites and other insects. This can be hazardous due to the relatively large amounts of high frequency power required to be transmitted in order to kill such insects. Furthermore, the microwaves are generally only used once the insects are detected which may be after the insects have inflicted large and noticeable amounts of damage to the building.

OBJECT OF THE INVENTION

It is an object of the present invention to provide a method and system for detecting pests, such as termites, by the use of microwaves.

Further objects will be evident from the following description.

DISCLOSURE OF THE INVENTION

In one form, although it need not be the only or indeed the broadest form, the invention resides in a method of detecting insects in a structure including the steps of:

transmitting a near field microwave signal into a part of the structure;

receiving a receive signal dependent on the near field signal; and processing the receive signal to provide an output signal indicative of the presence of the insects in the near field microwave signal.

In preference the step of transmitting a near field microwave signal involves transmitting a modulated signal. The modulation may be in amplitude, frequency or phase and is suitably in the audio range.

Preferably, the step of transmitting is further characterised by the near field microwave signal being less than 2 meters from a transmitter transmitting said signal. More preferably, the signal is less than 1 meter from the transmitter. Most preferably the transmitter is closely adjacent or abutting said part of the building, thereby the near field microwave signal is less than ½ meter from the transmitter. The step of transmitting may be further characterised by the near field signal being normal to said part of the structure.

Suitably, the near field microwave signal is circular polarized.

The receive signal is preferably a reflected signal.

Preferably, the method is further characterised by the steps of transmitting and receiving being effected by a common antenna. Suitably the antenna may be monostatic or bistatic. The antenna may be a horn, apertured printed circuit board, dish, or any other suitable antenna.

Suitably, in one aspect, the step of receiving includes the step of mixing the signal dependent on the near field signal with a reference signal to provide a receive signal which is a combined signal.

Suitably the combined signal comprises a beat frequency signal component.

The step of receiving a receive signal may involve receiving a signal synchronous with the modulation frequency of the transmitted signal.

Preferably, the step of processing may also include the steps of filtering and amplifying the receive signal. Filtering and amplifying may suitably maximise the beat frequency signal component.

Preferably, the step of filtering is characterised by the filtering being effected by a low pass filter having a cut-off frequency of less than 50 HZ. More preferably, the cut off frequency is less than 20 HZ and most preferably 10 HZ or less.

A band pass filter may suitably be used for the step of filtering in which the upper cut-off frequency may be any one of the above described values and the lower cut-off frequency being approximately 0.01 HZ.

In a further aspect of the invention the step of processing further includes the steps of digitizing and analysing the receive signal to provide said output signal or output data indicative of the presence of said insects in said near field microwave signal.

In a yet further form, the step of analysing may include analysis of spectral characteristics of the receive signal.

Suitably, said analysis of spectral characteristics includes Fourier transformation.

The step of processing the receive signal alternatively includes adaptive recognition of termite indicative signals. The adaptive recognition may suitably be performed in a neural network. A hidden Markov chain processor and/or a Kalman filter may suitably be employed at the input to the neural network to enhance the signal to noise ratio of the signal input to the neural network.

In a further form, the invention resides in a system for detecting insects in a structure, the system comprising:

signal generator means operatively coupled to transmitter means to thereby transmit a microwave signal into a part of a structure;

receiver means for receiving signals indicative of the presence or otherwise of insects in a near field of the microwave signal; and processor means for processing the received signal to provide an output signal indicating the presence or otherwise of insects.

The signal generator means is preferably a microwave generator means. A Gunn oscillator is a suitable signal generator means.

Preferably, said transmitter means is adapted to transmit a circular polarized field. The transmitter means preferably comprises a transmitting antenna which may be a horn, apertured printed circuit board, dish, or other suitable antenna.

The receiver means preferably comprises a receiving antenna which may suitably be the same as the transmitting antenna.

In preference the system further comprises modulator means operatively coupled to the signal generator means for modulating the transmitted microwave signal at a selected frequency.

The receiver means may suitably comprise a synchronous rectifier for locking on receive signals synchronous with the modulated transmitted microwave signal.

The receiver means further comprise mixing means operatively coupled to the receiving antenna and the signal generator means, said mixing means providing a receive signal dependent upon an indicative signal received from said receiving antenna and a reference signal from said signal generator. The receive signal is a combined signal.

In one form, the processor means includes filter means for filtering said combined signal, wherein said combined signal comprises a beat frequency component.

The filter means is suitably adapted to reject frequencies other than frequencies indicative of the presence of insects in the near field, such insects typically being termites.

Preferably, the filter means is a low pass filter having a cut-off frequency of less than 50 HZ. More preferably, less than 20 HZ and most preferably 10 HZ or less.

The filter means may be a band pass filter in which the upper cut-off frequency may be any one of the above frequencies and the lower cut-off frequency may be approximately 0.01 HZ.

The processor means may include amplification means for amplifying the combined signal which may be filtered by said filter means.

The processor means may suitably include digitizing means operatively coupled to a microprocessor for providing said output signal.

In one aspect the processor means is a microprocessor performing one or more of digitizing, amplifying and filtering tasks in software.

The microprocessor may be programmed with a neural network algorithm and/or a hidden Markov chain processor algorithm and, optionally, a Kalman filter. The microprocessor may also perform such tasks as analog to digital conversion, keypad reading and display control.

In preference, the system further comprises display means for displaying the output signal. The display means may be an audio output, a needle meter or a visual display unit.

BRIEF DETAILS OF THE DRAWINGS

To assist in understanding the invention preferred embodiments will now be described with reference to the following figures in which.

Figure 2:
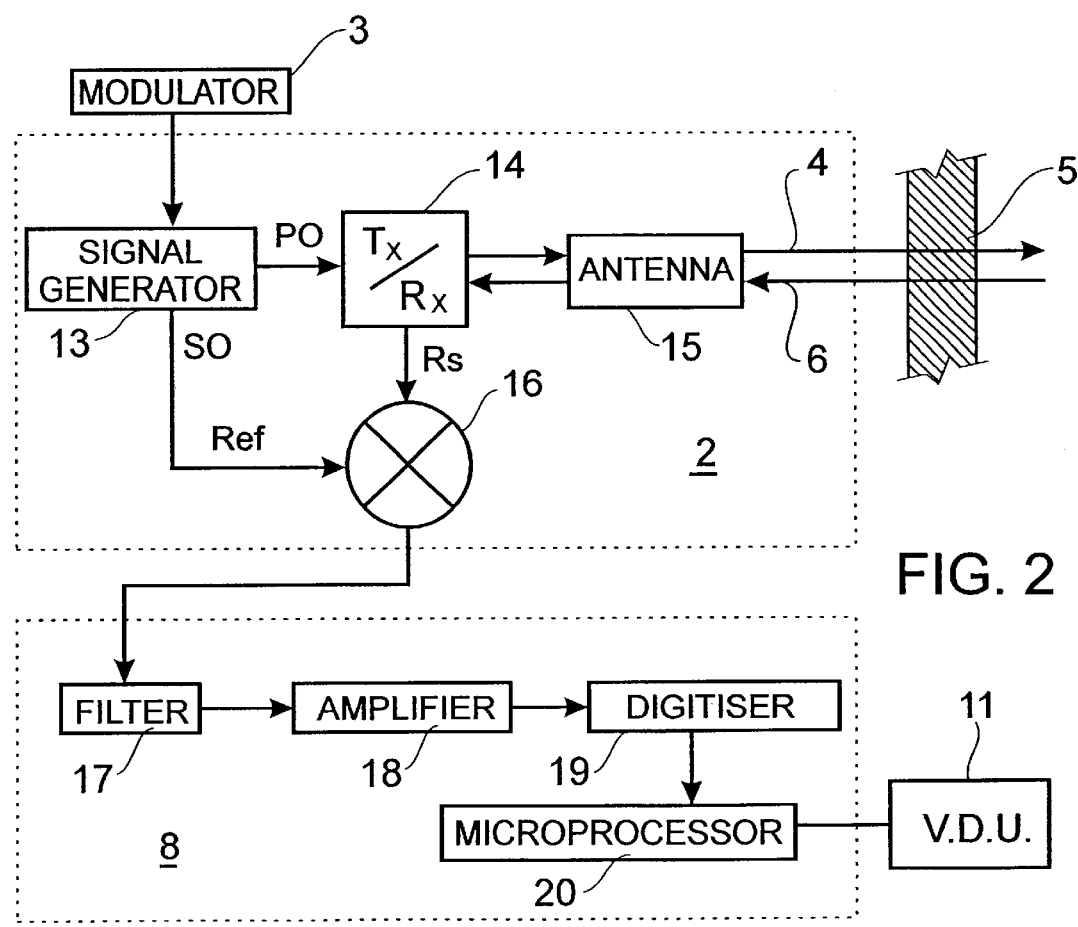
FIG. 2 is a block diagram of an insect detection system in accordance with the invention.
Figure 8A:
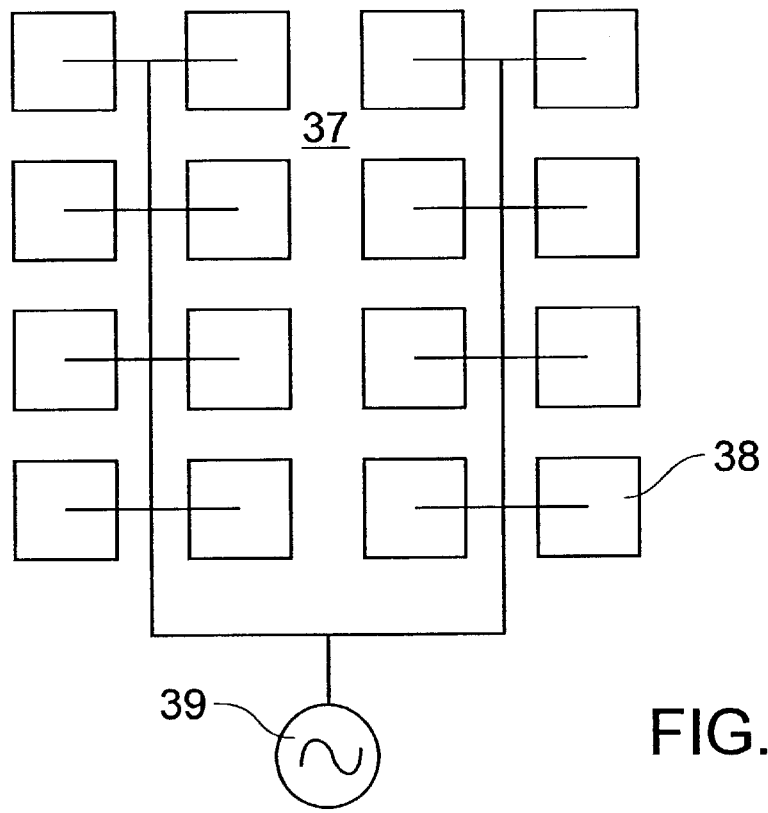
Figure 8B:
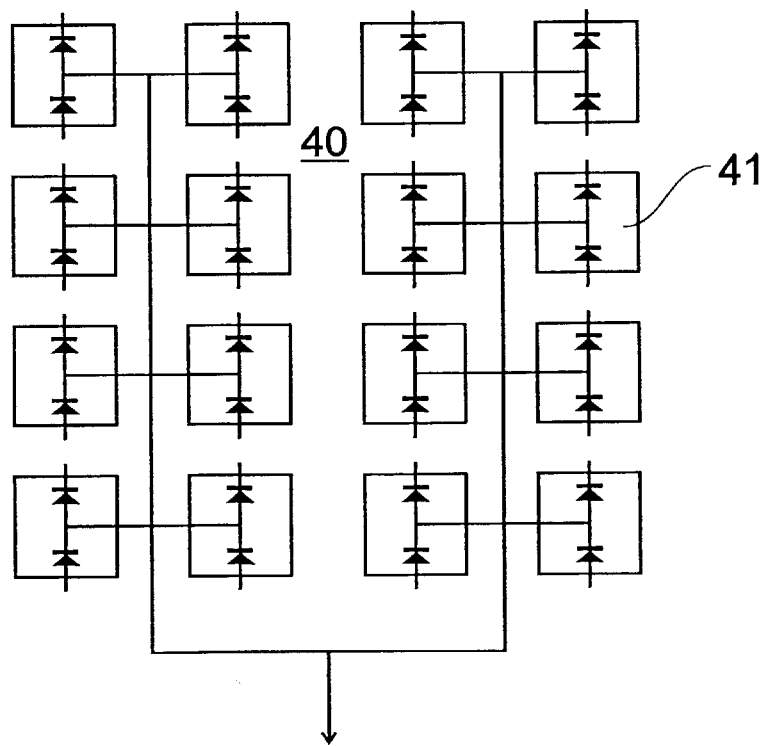
Figure 9:
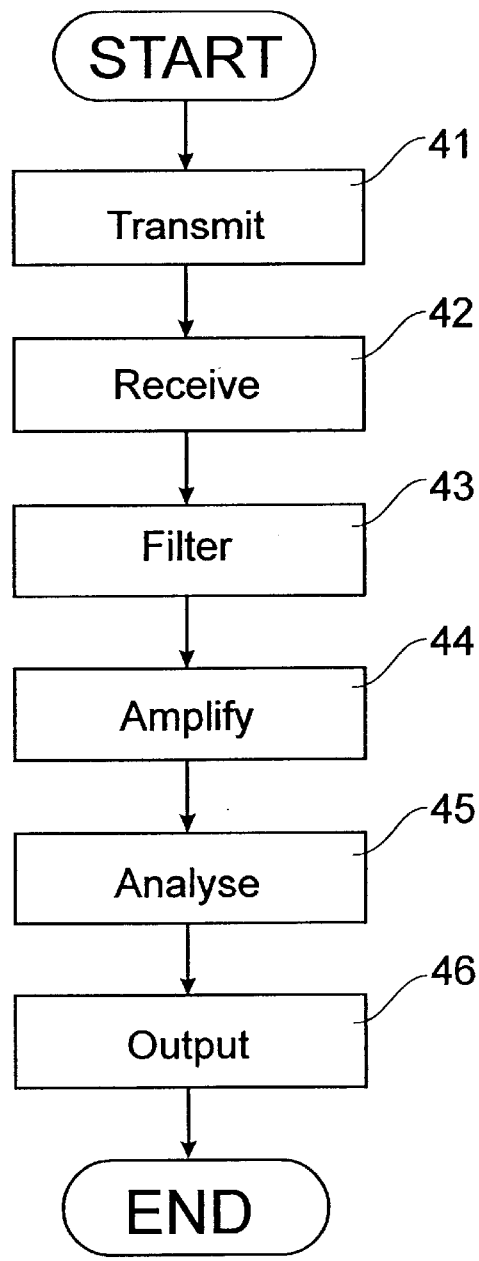
Figure 10:
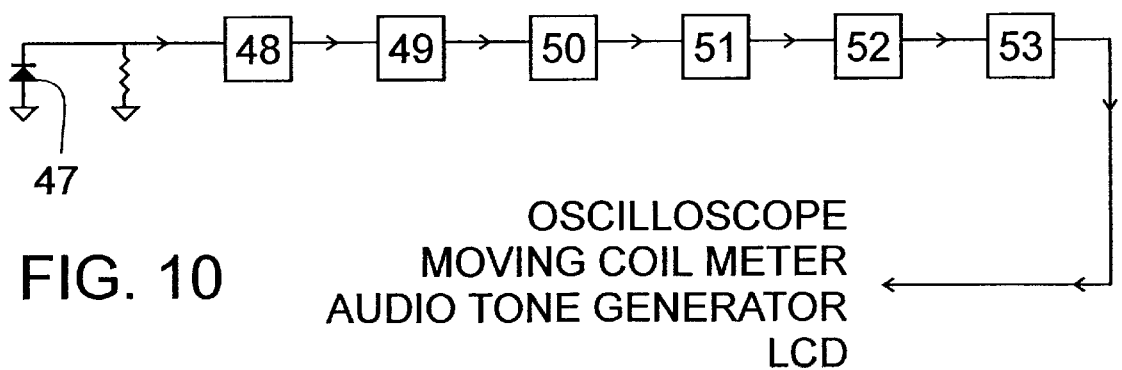
Figure 11A:
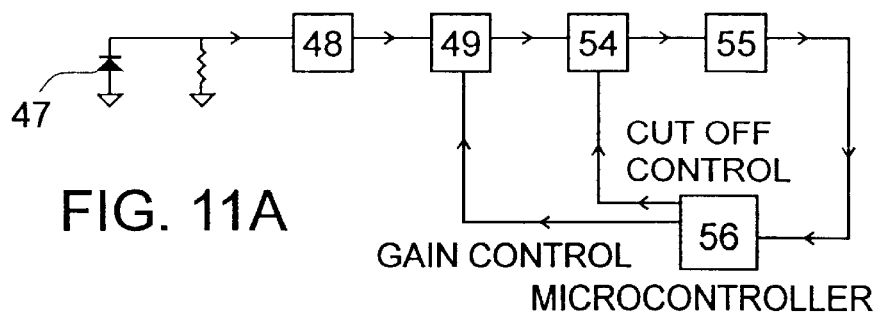
Figure 11B:
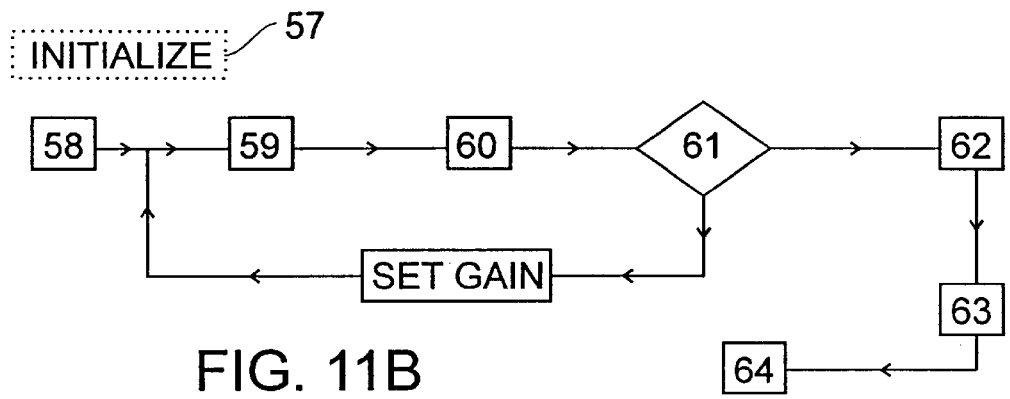
Figure 12A:
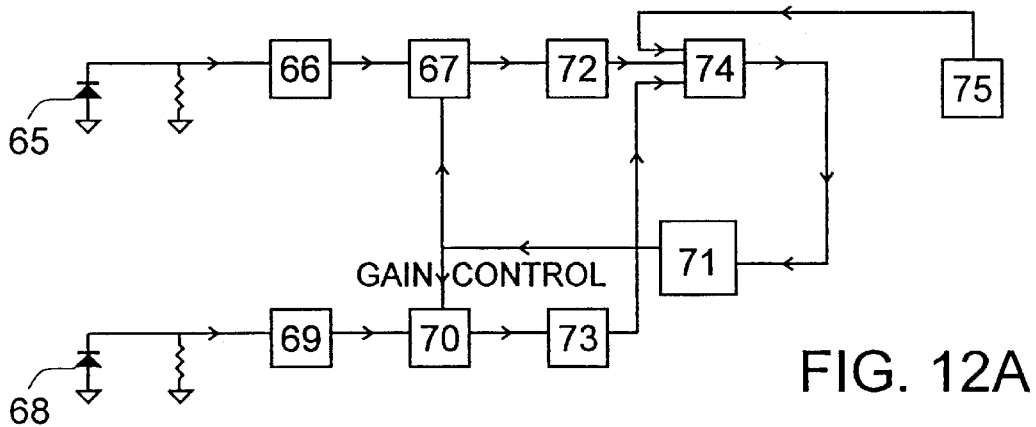
Figure 12B:
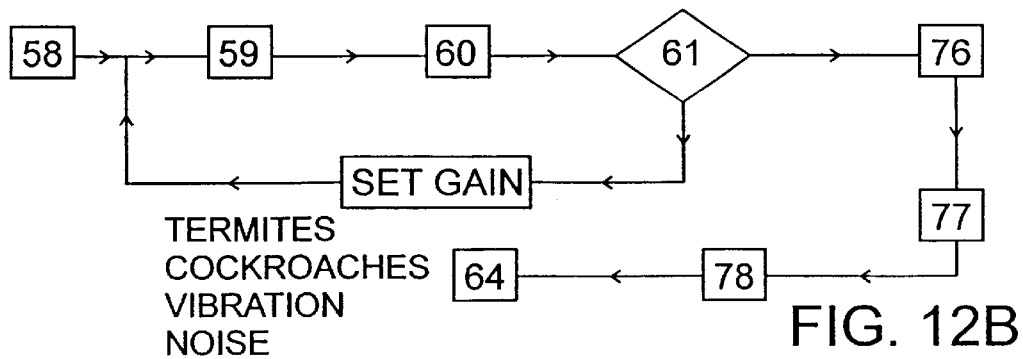
Figure 13:
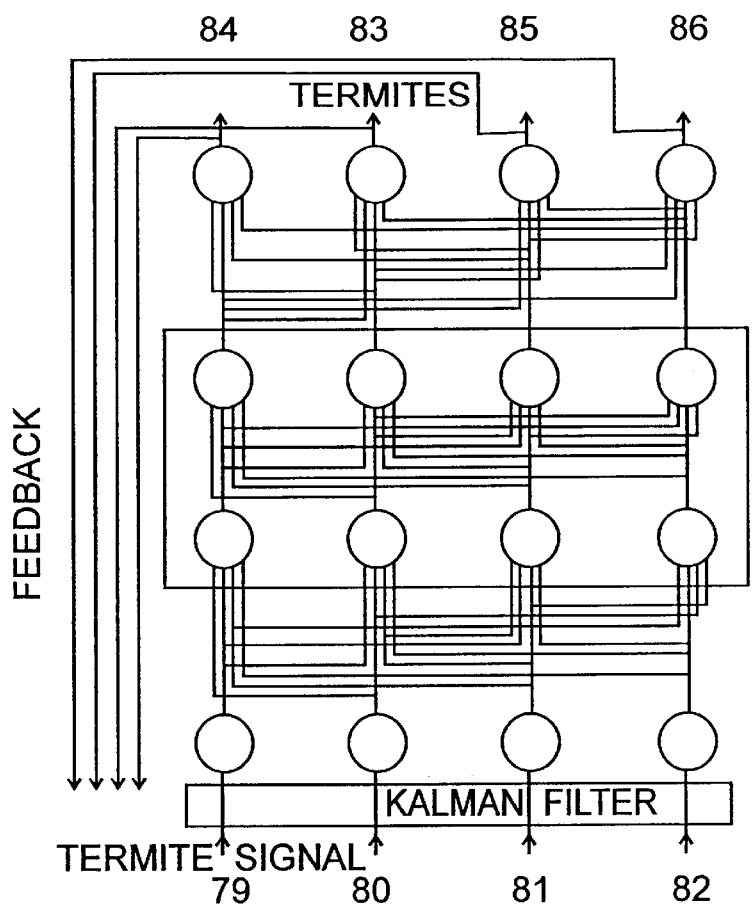
Figure 14A:
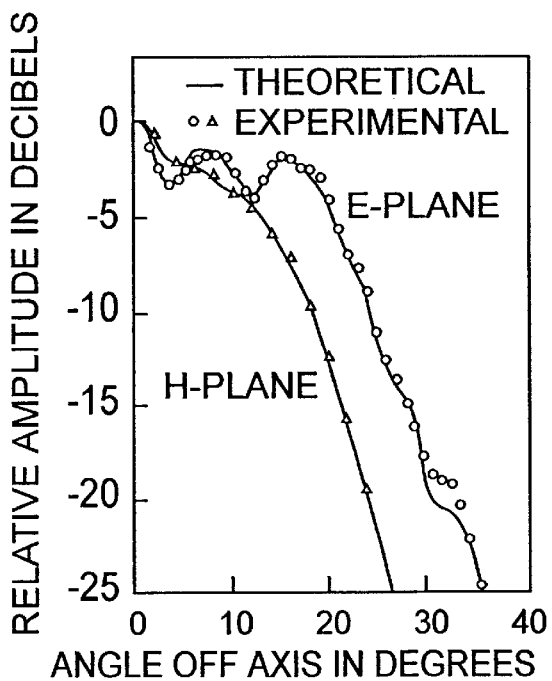
Figure 14B:
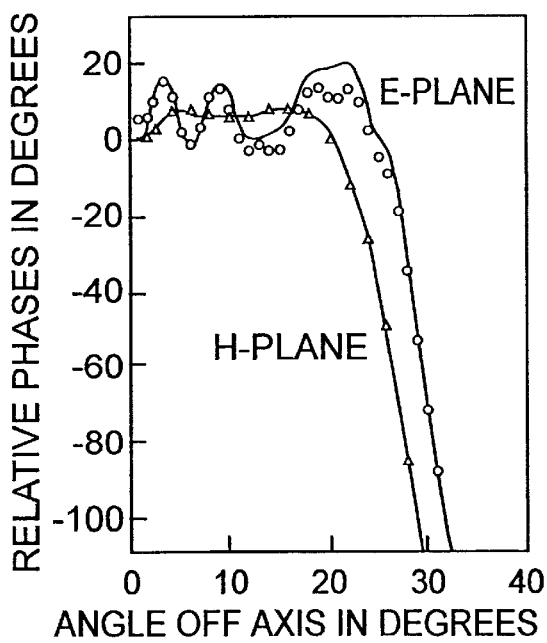
Figure 15:
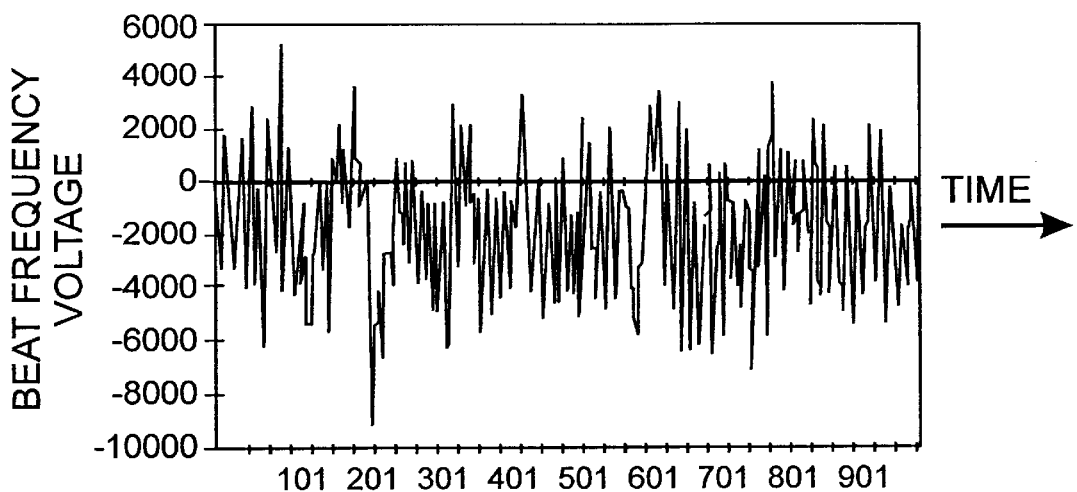
Figure 16:
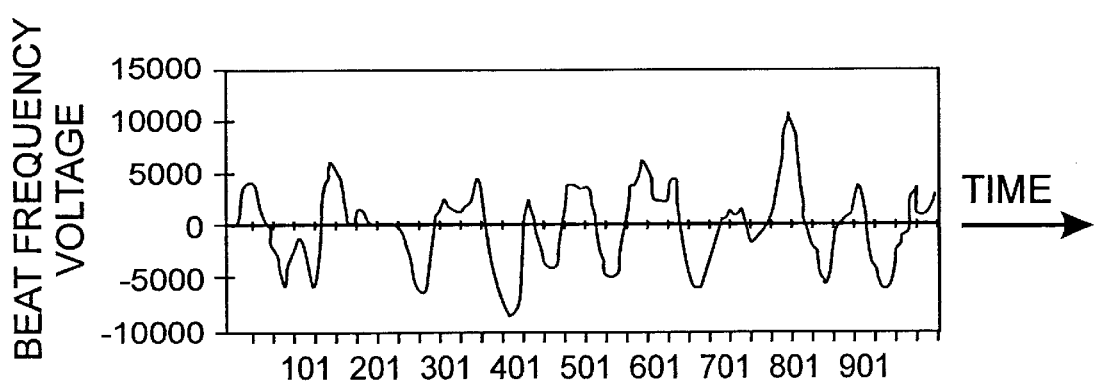
Figure 17:
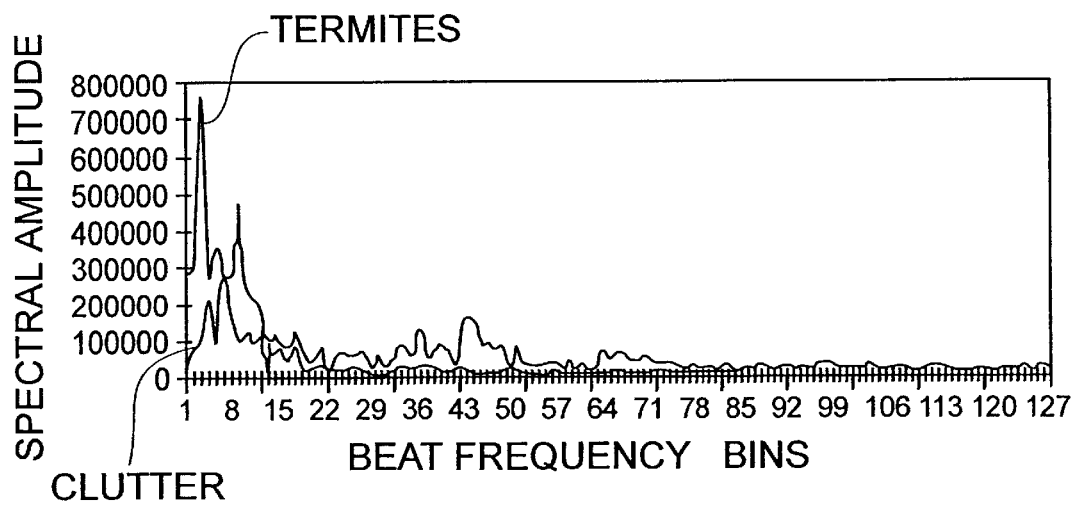

FIGS. 8A–B depicts a planar antenna array;

FIG. 9 is a flow diagram illustrating how the system of FIG. 2 detects insects such as termites, FIG. 10 shows a hardware block diagram for analogue signal processing;

FIGS. 11A–B shows a hardware block diagram and software flowchart for Fourier signal processing;

FIGS. 12A–B shows a hardware block diagram and software flowchart for adaptive recognition signal processing;

FIG. 13 is a block diagram of a neural net pattern recognition processor and hidden Markov chain processor with optional Kalman filter;

FIGS. 14A–B are plots of near field microwave radiation patterns;

FIG. 15 is a graph showing the output of FIG. 2 when no insects are present in a near field signal;

FIG. 16 shows the output of FIG. 2 indicative of insects in a near field signal, and FIG. 17 shows a Fourier transform of FIGS. 15 and 16.

In the drawings, like reference numerals refer to like parts.

DETAILED DESCRIPTION OF THE DRAWINGS

Figure 1:
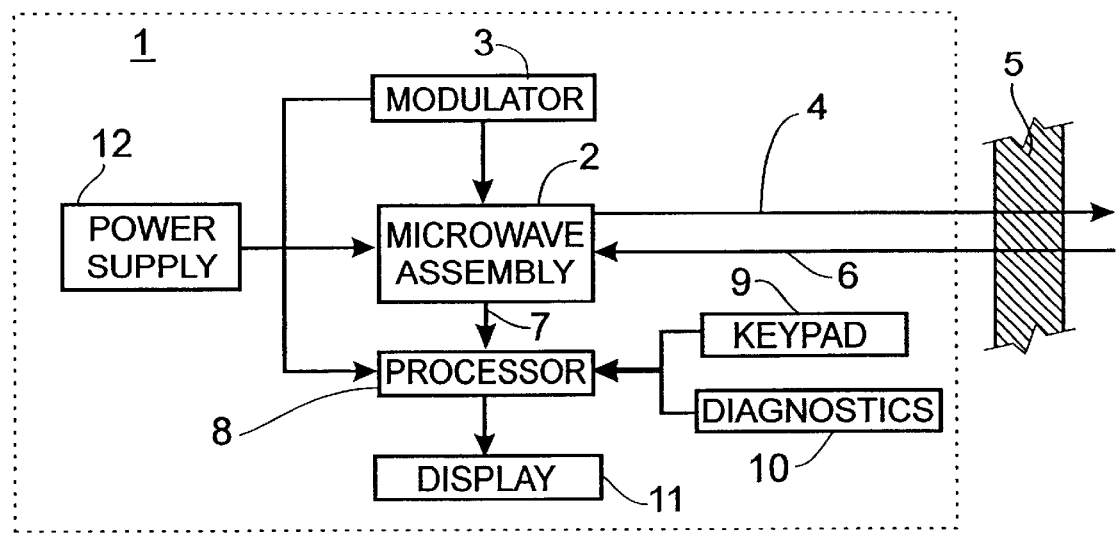
FIG. 1 is a block diagram of a system for detecting insects.

Referring to FIG. 1, there is shown a conceptual block diagram of a system 1 for detecting insects, such as termites. The system 1 comprises a microwave assembly 2 that transmits a continuous wave microwave signal at a frequency of (for example) 24.125 GHz. The signal may be modulated by modulator 3.

Signals 4 are transmitted into region 5 to detect the presence or otherwise of termites or other insects. Reflected signals 6 are received by the microwave assembly 2. Receive signals 7 are passed to a processor 8 that performs the signal processing. Commands and programming may be input to the processor 8 from the (optional) keypad 9 or from various (optional) diagnostics 10. The output from the processor 8 is displayed on display 11. The display is shown as a visual display unit although in other embodiments it may be, for example, a meter or liquid crystal display. A power supply 12 provides power to elements of the system 1.

Referring to FIG. 2, the elements of the microwave assembly 2 and processor 8 are shown in more detail. The microwave assembly includes a signal generator 13 for generating the signal of 24.125 GHZ at a primary output PO of signal generator 13. Primary output PO is connected to a receiver and transmitter unit (or circulator) 14 which is coupled to antenna 15. The receiver/transmitter unit 14 and antenna 15 may be incorporated in a rectangular horn antenna which operates as both a transmitter and receiver. In use, the antenna is located closely adjacent or in an abutting relationship with the region 5, which is most often a wall but may be another part of the structure. Antenna 15 has a face covered with tinted plastics material which acts as a radome.

A secondary output SO of signal generator 13 provides a reference signal, Ref, to one input of a mixer 16. The other input of mixer 16 is connected to the receiver circuitry of the receiver/transmitter unit 14, from which a received signal Rs is provided.

Mixer 16 combines reference signal Ref and received signal Rs to provide a combined signal Cs comprising a beat frequency component at the output of mixer 16. The combined signal Cs corresponds to signal 7 of FIG. 1.

FIG. 2 also includes details of processor 8 having an input connected to the output of mixer 16. Processor 8 includes a band pass filter 17 having a lower cut-off frequency of approximately 0.1 HZ and an upper cut-off frequency of 10 HZ.

An output of filter 17 is connected to an amplifier 18, the output of which is connected to an analogue to digital converter 19. A microprocessor 20 is coupled to converter 19 to receive and process digitized data from converter 19 and display an output signal or data indicative of the presence of insects on a visual display unit 11. Other inputs may be provided to microprocessor 20 as indicated in FIG. 1. An adaptive filter may be used to suppress clutter or to render the process specific to particular insects. The processor 8 may be embodied in a personal computer with the filter, amplifier and digitizing functions being performed in software or partially in software.

Figure 3:
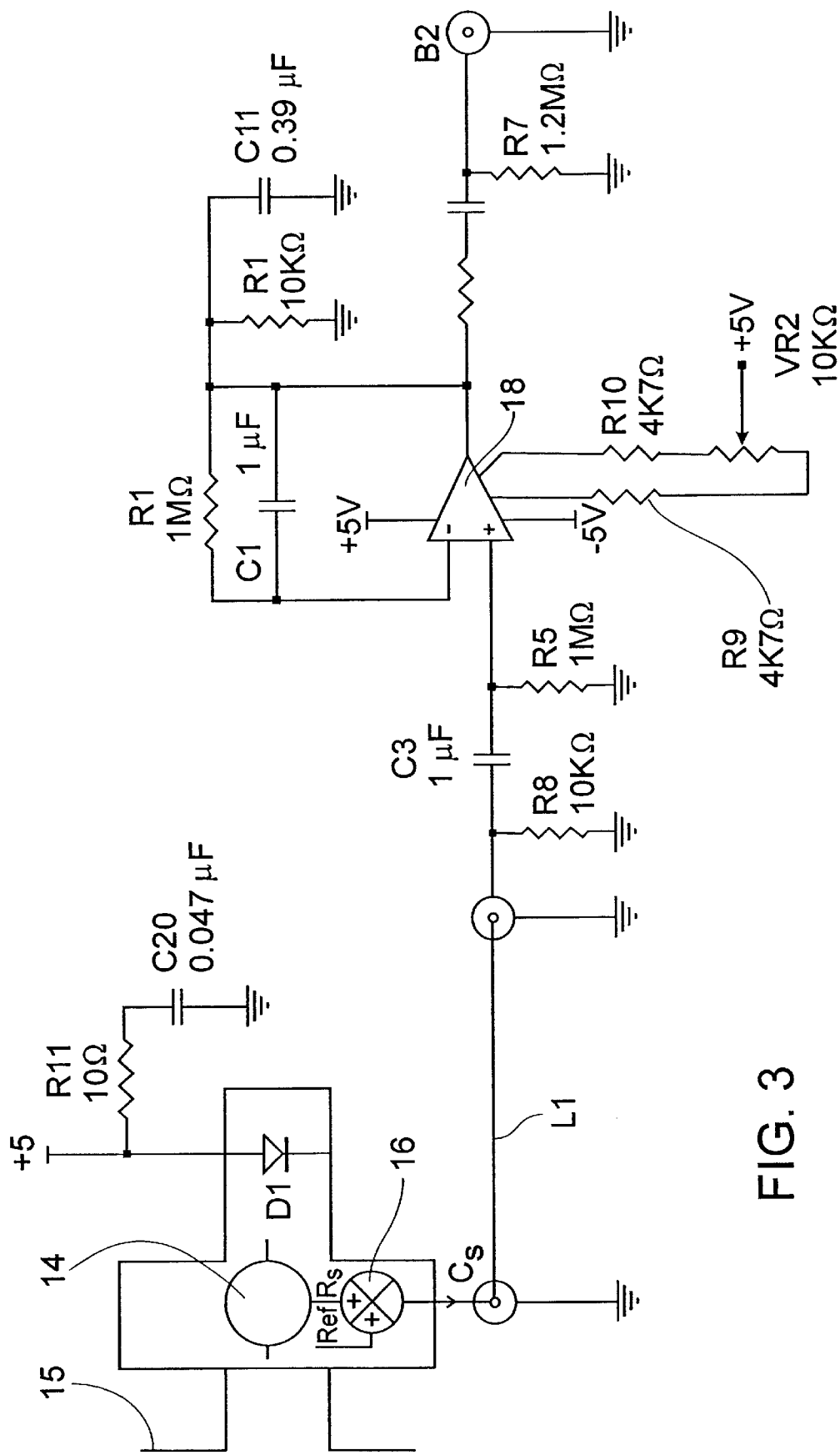
FIG. 3 is a circuit diagram of FIG. 2.

Referring to FIG. 3, there is illustrated a circuit diagram 21 corresponding to the microwave assembly 2 and processor 8 of FIG. 2 and therefore identical components have the same number. Circuit diagram 21 includes an oscillator diode D1 for providing the 24.125 GHZ signal to antenna 15 via a circulator 14. Anode of diode D1 is connected to a +5 volt power line and diode D1 is in parallel with a series resistor capacitor filter network R11, C20 which reduces the effects of power line oscillations.

Circulator 14 isolates the mixer 16 from the oscillator signal by a factor of approximately 200. This provides a leakage signal from circulator 14 resulting in a reference signal Ref of 24.125 GHZ to mixer 16. Accordingly, reference signal Ref is synchronised to and is the same frequency as the signal transmitted by antenna 15 which, in the absence of target motion results in a beat frequency of 0.0 HZ.

Output of mixer 16 is connected to a co-axial cable link L1 coupling mixer 16 to a high pass filter network of capacitor C3 and resistor R5 which has a cut-off frequency of 0.1 HZ. Furthermore, there is a resistor R8 which is a DC return resistor for mixer 16. Currents from subsequent circuitry are DC blocked by capacitor C3.

The common node of capacitor C3 and resistor R5 are connected to an operational amplifier 18 the gain of which is dependent upon feedback resister R1 in which capacitor C1 provides filtering. Further, parallel resistor and capacitor network R2, C11 at the output as operational amplifier 18 provide a low pass filter having a cut off frequency of approximately 10 HZ. Additional filtering and D.C. blocking are provided by resistor capacitor network R6, C2 and R7 in which common node of C2 and R7 is connected to a co-axial cable port B2 for connection with digitizer 19 of FIG. 2.

Operational amplifier 18 has +/-5 volt power rails supplied by standard power supplies. The +5 volt power rail of diode D1 is supplied from the same power supply. Resistors R9, R10 and VR2 located between pins one and eight of operation amplifier 18 are used to select an appropriate offset voltage.

Figure 4:
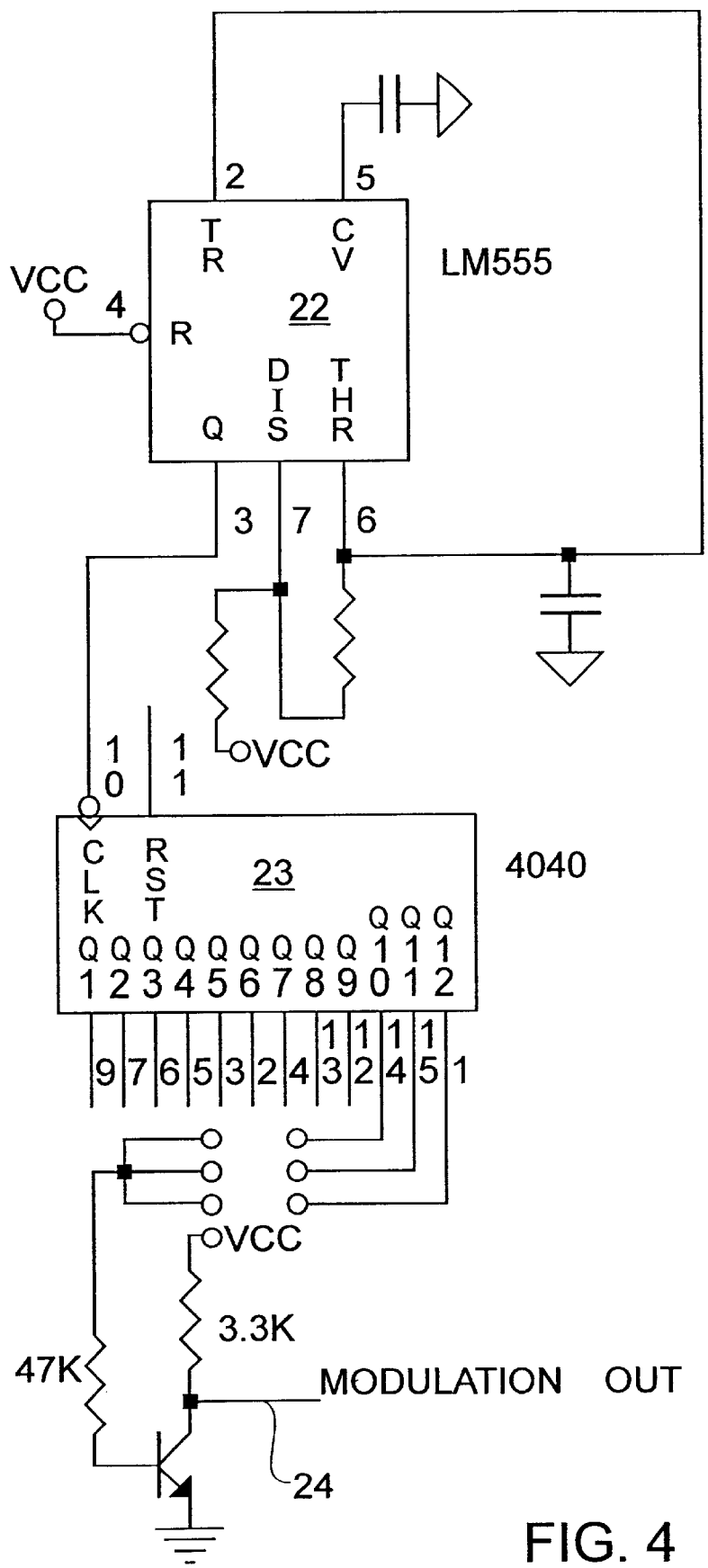
FIG. 4 is a circuit diagram of the modulator of FIG. 1.

A detailed schematic circuit diagram of one embodiment of the modulator 3 is shown in FIG. 4. An LM555 timer 22 provides a driving frequency of around 1 kHz. This frequency is chosen to be well removed from the mains frequency of 50 Hz and power line harmonics. It also reduces 1/f noise in the first receiver amplifier. A 4040 flip-flop 23 is used to divide the fundamental oscillator frequency for a 50% duty cycle. The output 24 from the modulator 3 drives the signal generator 13 in the microwave assembly 2.

Figure 5:
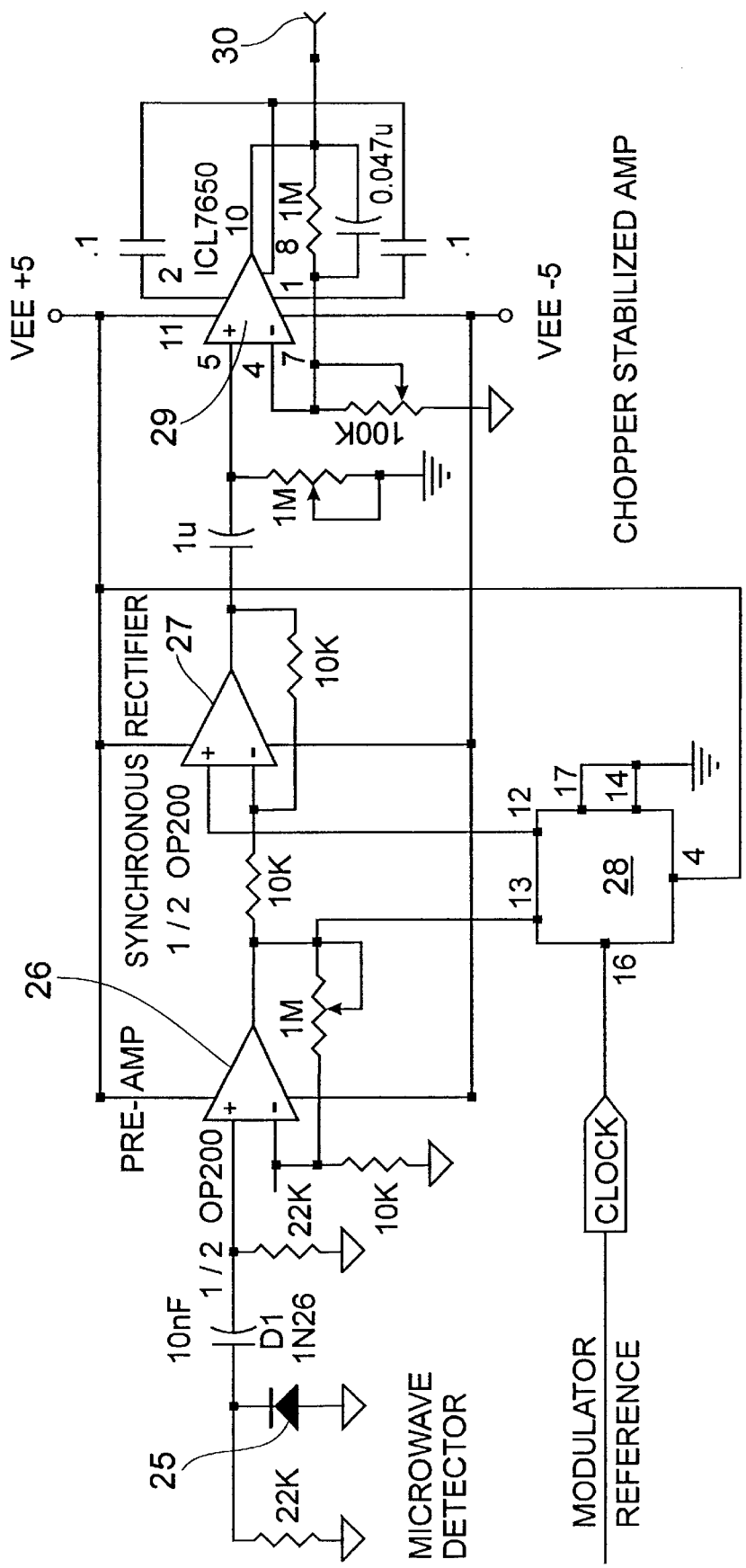
FIG. 5 is a circuit diagram of the receiver of FIG. 1.

The above embodiments have described simple microwave assemblies incorporating mixer detection. Other signal receiving schemes which take advantage of the optional modulator may also be employed. A circuit diagram for one alternate embodiment of a receiver is shown in FIG. 5. A reflected signal is received by microwave diode 25. The microwave diode detected signal consists of a large bias and a small, superimposed signal due to the termites. The total signal is first amplified using a high pass filter 26 with a cut-in of around 100 Hz. A gain of 10 is chosen to provide an almost square wave output of +/-3 volts without saturating the first amplifier 26.

The signal is amplified in a synchronous amplifier 27 whose gain is toggled between +1 and -1 in phase with the modulation from the modulator 3. The switching is performed by an LTC1043, 28. Any signal that is synchronous with the modulating frequency results in a DC output from the synchronous amplifier 27. The output from the synchronous amplifier 27 is passed through a narrow band, low offset (chopper stabilized) amplifier 29. A passband of 0.1–10 Hz is selected. The output 30 of the receiver is passed to the processor 8 or may be passed directly to the microprocessor 20.

Figure 6:
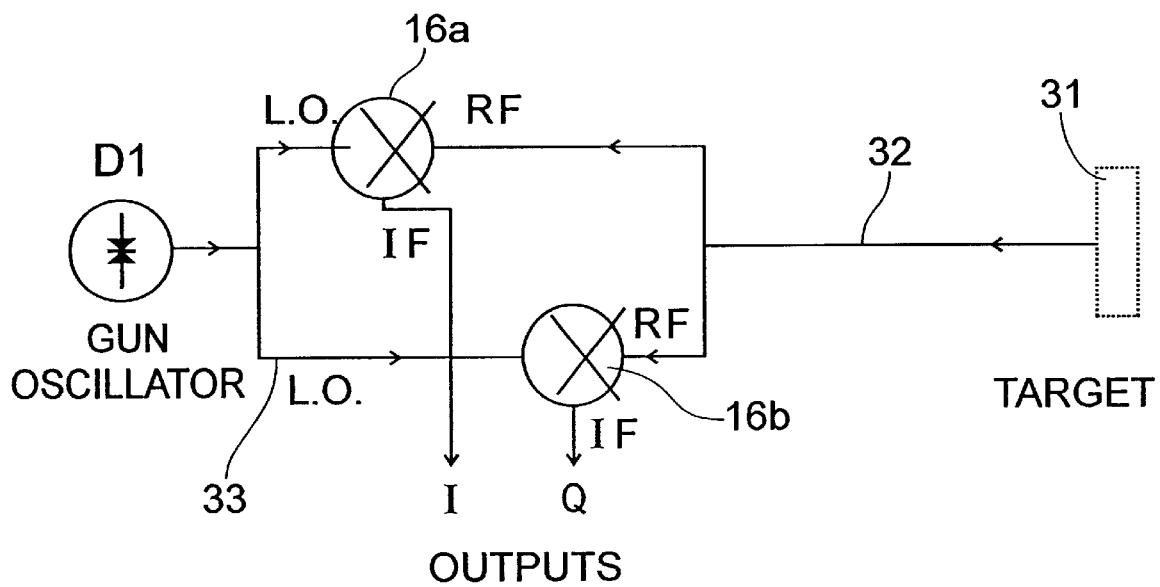
FIG. 6 depicts an IQ mixer configuration.

An alternate mixer embodiment is shown in FIG. 6. As with the embodiment of FIG. 3 a microwave signal is generated and transmitted towards a target 31. The reflected signal 32 is mixed with a reference signal 33 from the diode D1. The Q mixer is phased such that the output is leading (or lagging) that of the I mixer by 90°. Motion of the target 31 towards the microwave assembly produces circular rotation of a trace on an oscilloscope configured for XY display of the two inputs I and Q. Motion away from the microwave assembly produces rotation of the opposite sense. Pure amplitude modulation (AM) appears as a straight line of unity gradient. Amplitude Modulation combined with motion results in erratic trajectories with or without rotation. A skilled operator can recognise the oscilloscope trace to identify the presence or otherwise of termites or other insects in the target area.

Figure 7:
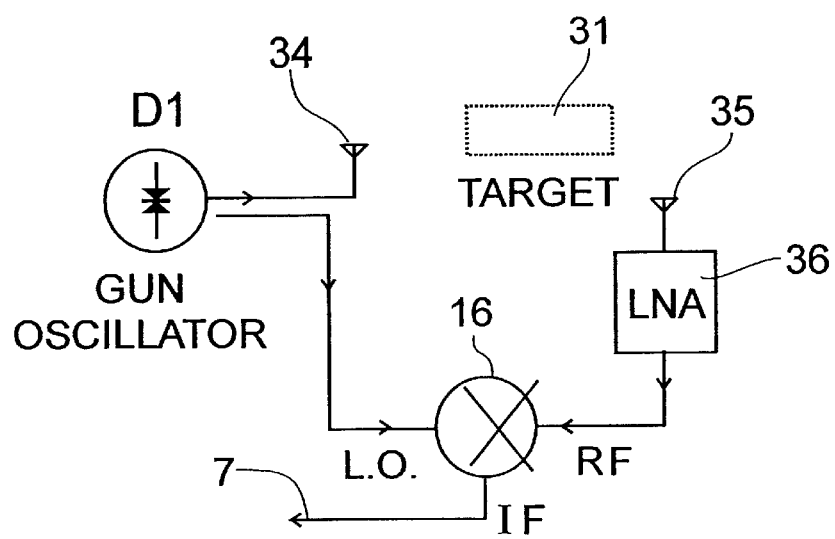
FIG. 7 depicts a bistatic radar configuration.

A bistatic radar configuration is depicted in FIG. 7 for use in the invention. In this embodiment the transmitting antenna 34 is separated from the receiving antenna 35. A low noise amplifier 36 provides initial amplification of the reflected signal before passing to the mixer 16. The low noise amplifier 36 is suitably a monolithic microwave integrated circuit (MMIC) with a maximum gain of about 10 dB. Careful positioning of antennas 34 and 35 can minimise the effect of interference due to elements of the structure between the microwave assembly and the target termites. The intermediate frequency output 7 is passed to the processor 8 as described earlier.

A planar antenna array configuration is depicted in FIG. 8. FIG. 8A depicts a transmitting array 37 comprising sixteen transmitting antennas, such as 38, coupled to microwave source 39, which could be a microwave diode. The receiver array 40 depicted in FIG. 8B comprises sixteen receiving antennas, such as 41. The planar array configuration has the advantage that the signals can be combined from a number of antenna elements to imitate beam steering and focussing. This can be done with either or both of the transmitter array 37 and receiving array 40. Furthermore, redundancy and non-redundancy of signals from different antenna apertures can be used to enhance desired signals over the clutter. A planar antenna structure is also easy to manoeuvre behind obstacles, such as cupboards, and covers a larger area than a single element. In this embodiment the control of the array can be effected by the microprocessor 20.

Referring to FIG. 9, the method of using the system of FIG. 1 is illustrated in a flowchart. The method is worked with an antenna located closely adjacent to a wall which is suspected to contain termites. A microwave field is transmitted at step 41 from a microwave assembly towards and through the wall. A reflected signal dependent upon near field activity (ie. Movement or presence of termites in the wall) is received at step 42. This received signal is mixed with a reference signal to provide a combined signal having a beat frequency which is filtered at step 43 to select frequencies indicative of the presence of termites. The filtered signal is then amplified at step 44. Steps 43 and 44 may be interchanged depending on the nature and magnitude of the signal or pre-amplification may be employed prior to filtering. The resulting signal is then analysed at step 45 and output to some form of display at step 46. The display may be hard copy, oscilloscope(s), light emitting diode(s) or audio signal(s).

Steps 43, 44 and 45 constitute the signal processing which can be performed according to a number of preferred embodiments. Three preferred embodiments are basic analog signal processing, fixed algorithm spectral recognition and adaptive recognition.

FIG. 10 depicts a hardware block diagram for basic analog signal processing. The output of a microwave mixer 47 is coupled to a pre-amplifier 48 and lock-in amplifier 49. The lock-in amplifier 49 locks in to signals having a modulation frequency applied by modulator 3 (refer FIG. 1). A filter arrangement comprising a high pass filter 50 and low pass filter 51 select signals in a frequency range indicative of termites. Some analog signal processing occurs in display equaliser 52 before a final stage amplifier 53 amplifies the signal for display on an oscilloscope, moving coil meter etc.

FIG. 11 depicts a hardware block diagram (FIG. 11A) and software flowchart (FIG. 11 B) for a signal processing approach in which a fixed algorithm is employed to process the signal and compare it with stored templates to identify spectral components indicative of termites. As with the previous embodiment the signal from the microwave mixer 47 is passed to pre-amplifier 48 and lock-in amplifier 49. The signal is filtered in anti-alias filter 54 and digitised in ADC 55. The digital signal is passed to microprocessor 56 for signal processing.

The signal processing is depicted in the flowchart of FIG. 11B. All parameters are initialised 57 and an appropriate initial gain and software controlled digital filter bandpass are set 58. The software controlled gain and filter bandpass are set to remove as much of the interference and noise, such as 50 Hz and harmonics, as possible, without affecting the Doppler and AM signal from the insects and vibration. This can be effectively achieved by computing the windowed covariance of the data time series to determine power spectral density. Ten seconds of data is acquired 59 and a FFT is performed 60. A check of the magnitude and frequency of the FFT data is made 61 and if necessary the gain at 58 is adjusted and new data is acquired. If the data at 61 is within parameters it is compared with stored templates 62. The closest match is determined 63 and displayed 64. This embodiment provides a good discrimination between real signals and noise at a minimal hardware an software cost.

A more sophisticated signal processing embodiment is described with reference to FIG. 12 which includes a hardware block diagram in FIG. 12A and a software flowchart in FIG. 12B. In this embodiment the IQ mixer embodiment of FIG. 6 is employed. The signal from the I channel mixer 65 is passed to pre-amplifier 66 and lock-in amplifier 67. Similarly the signal from the Q channel mixer 68 is passed to pre-amplifier 69 and lock-in amplifier 70. The lock-in frequency is provided by microprocessor 71. The gain of the lock-in amplifiers 67, 70 is software controlled to set the gain to maximise the resolution of the analog to digital converters.

Respective anti-alias filters 72 and 73 provide filtering before digitiser 74. Signals from a vibration sensor 75 are also directed to the digitiser 74. The digitised signals are passed to microprocessor 71 for analysis.

Steps 58 to 61 are identical to the steps performed in the prior embodiment. At step 62, as much of the vibration induced signal is removed as possible. This can be done by passing the signal through a neural net configured as an adaptive filter. The LMS (least mean square) algorithm for determining tap weights developed by Widrow is a suitable example. This is linear, recursive filter which requires an initial template of a vibration induced signal. It passes the received signal through a filter tuned to remove the template-like signal, computes an RMS residual vibration-like signal and estimates new tap weights for the filter coefficients. It performs multiple passes, with new estimates, until the LMS residual shows no further The microprocessor 35 implements a neural net algorithm and a hidden Markov chain processor with optional Kalman filter as represented schematically in FIG. 2. Signals from the receiver 33 are input at 40. Other signals can also be input such as vibration sensor signals 41, ambient noise signals 42 and reference signals stored in memory 43 for comparison.

The neural net algorithm performs pattern recognition on the signal by finding a best fit to stored signal templates. It does so by a learning process, using input, output and hidden layers as analogues of neurons and synapses.

The outputs from the algorithm include, for example, indications of termites 44, cockroaches 45, vibrations 46 and noise 47. The number of hidden layers required is determined empirically in a neural net development system. The training of the net depends on the depth of the data base and variations between signals of recognised termites. Details on neural nets can be found in "Neural Network PC Tools, A Practical Guide", edited by R C Eberhart and Roy W Robbins, Academic Press Inc 1990, ISBN 0-12-228649-5.)

Also indicated in FIG. 13 is a Hidden Markov chain processor. Further details of the operation and implementation of hidden Markov algorithms may be found in "Frequency Tracking using Hidden Markov Models with Amplitude and Phase Information" by Ross F Barrett and David A Holdsworth which appeared in IEEE Transactions on Signal Processing, vol 41, no. 10, October 1993, pp 2965–2976.

Hidden Markov Model tracking is achieved by obtaining overlapping FFT's of the signal time series and assigning probabilities to causal relationships between frequency bins in adjacent FFT's. Eventually deterministic signals are all that survive this process and the probabilities of tracking such events tend to 1.

An alternative indicated in FIG. 13 is a Kalman filter. The Kalman filter uses position and velocity measurements to predict new values and compare them with actual new measurements in order to obtain a better estimation. Kalman filter techniques have been applied in various radar tracking applications and may be adapted for tracking termites or groups of termites. The Hidden Markov Model or Kalman filter tracking algorithms may be used as alternative processes to enhance the signal quality before the pattern recognition by the neural net.

FIG. 14*a* and FIG. 14*b* show representative near field microwave antenna patterns. Insect motion is detected by small changes in the amplitude and phase of reflected signals. It is speculated that two insect related mechanisms lead to detectable signals. These are:

(a) insects moving into the field of view or tracing out fluctuations in the near field amplitude pattern or providing a changing reflection facet back to the radar assembly. This echo can be observed for any insect motion with respect to the radar.

(b) the Doppler effect due to insect motion across the near field equi-phase contours. This is the effect used in police radar speed detectors.

Both of these effects are manifest in the frequency range from 0.1 Hz to 10 Hz. The reflection signal strength is believed to be related to:

1. The microwave properties of the insect (ie. dielectric constant and absorption coefficient);
2. The size/wavelength ratio of the insect;
3. The separation between the radar assembly and the insect;
4. The angle to the insect relative to the radar assembly boresight;
5. The properties of any intervening materials; and
6. The microwave polarization.

It will be appreciated from a consideration of FIG. 14a and FIG. 14b that the near field equi-phase contours are curved with significant wiggles. It is extremely unlikely that an insect would follow such a curved and convoluted path and therefore must produce phase shifts due to motion through the microwave field. In the case of termites there will always be some signal since termites are always moving and will therefore produce amplitude and phase shifts in the reflected signal.

As shown in FIG. 4 when the near field 24.125 GHZ signal is transmitted into a non-infested part of a building, random noise or clutter is dominant at the output of amplifier 7. However as shown in FIG. 5, when the near field 24.125 GHZ signal is transmitted into a termite infested part of a building the resultant signal at the output of amplifier 7 is indicative of the presence of termites. The resultant signal is much larger and is displayed at a lower sensitivity as is evident by the low level of fluctuations. Furthermore, the graph of FIG. 6 shows that when a Fourier transform of the signals from FIGS. 4 and 5 is undertaken, it is apparent that termites can be detected by the spectral characteristics at the output of amplifier 7. Finally, because signal attenuation can be strongly dependent upon wall anisotropy it is beneficial to use a circular polarised transmitted signal.

Throughout the specification the aim has been to describe the preferred embodiments of the invention without limiting the invention to any one embodiment or specific collection of features.

What is claimed is:

1. A method of detecting insects in a structure including the steps of: transmitting a near field microwave signal into a part of the structure; receiving a receive signal dependent on the near field signal; and processing the receive signal to provide an output signal indicative of the presence of the insects in the near field microwave signal.

2. The method of claim 1 wherein the step of transmitting a near field microwave signal involves transmitting a modulated signal.

3. The method of claim 1 wherein the step of transmitting is further characterised by the near field microwave signal being less than 2 meters from a transmitter transmitting said signal.

4. The method of claim 3 wherein the transmitter is closely adjacent said part of the structure.

5. The method of claim 1 wherein the step of transmitting is further characterised by the near field signal being normal to said part of the structure.

6. The method of claim 1 wherein the near field microwave signal is circular polarized.

7. The method of claim 1 wherein the receive signal is a reflected signal.

8. The method of claim 1 wherein the method is further characterised by the steps of transmitting and receiving being effected by a common antenna.

9. The method of claim 1 wherein the step of receiving includes the step of mixing the signal dependent on the near field signal with a reference signal to provide a receive signal which is a combined signal.

10. The method of claim 9 wherein the combined signal comprises a beat frequency signal component.

11. The method of claim 2 wherein the step of receiving a receive signal involves receiving a signal synchronous with the modulation frequency of the transmitted signal.

12. The method of claim 1 wherein the step of processing includes the steps of filtering and amplifying the receive signal.

13. The method of claim 12 wherein the step of filtering is characterised by the filtering being effected by a low pass filter having a cut-off frequency of less than 50 HZ.

14. The method of claim 12 wherein the step of filtering is characterised by the filtering being effected by a band pass filter having an upper cut-off frequency of less than 50 HZ and a lower cut-off frequency of greater than 0.01 HZ.

15. The method of claim 1 wherein the step of processing further includes the steps of digitizing and analysing the receive signal to provide said output signal indicative of the presence of said insects in said near field microwave signal.

16. The method of claim 15 wherein the step of analysing includes analysis of spectral characteristics of the receive signal.

17. The method of claim 15 wherein the step of analysis includes an analysis of spectral characteristics by Fourier transformation.

18. The method of claim 1 wherein the step of processing the receive signal includes adaptive recognition of termite indicative signals.

19. The method of claim 18 wherein the adaptive recognition is performed in a neural network.

20. The method of claim 18 wherein the adaptive recognition is performed in a neural network and a hidden Markov chain processor algorithm and/or a Kalman filter algorithm are employed at the input to the neural network to enhance the signal to noise ratio of the signal input to the neural network.

21. The method of claim 1 further including the step of displaying the output signal.

22. A system for detecting insects in a structure, the system comprising:

signal generator means operatively coupled to transmitter means to thereby transmit a near field microwave signal into a part of a structure;

receiver means for receiving signals indicative of the presence or otherwise of insects in a near field of the microwave signal; and processor means for processing the received signal to provide an output signal indicating the presence or otherwise of insects.

23. The system of claim 22 wherein said transmitter means is adapted to transmit a circular polarized field.

24. The system of claim 22 wherein the transmitter means comprises a transmitting antenna.

25. The system of claim 22 wherein the receiver means comprises a receiving antenna.

26. The system of claim 22 wherein the transmitter means and the receiver means comprise a common antenna.

27. The system of claim 22 wherein the system further comprises modulator means operatively coupled to the signal generator means for modulating the transmitted microwave signal at a selected frequency.

28. The system of claim 27 wherein the receiver means comprises a synchronous rectifier for locking on receive signals synchronous with the modulated transmitted microwave signal.

29. The system of claim 22 wherein the receiver means comprises a receiving antenna and further comprises mixing means operatively coupled to the receiving antenna and the signal generator means, said mixing means providing a receive signal dependent upon an indicative signal received from said receiving antenna and a reference signal from said signal generator.

30. The system of claim 22 wherein the processor means includes filter means for filtering said receive signal.

31. The system of claim 30 wherein the filter means is suitably adapted to reject frequencies other than frequencies indicative of the presence of insects in the near field.

32. The system of claim 30 wherein the filter means is a low pass filter having a cut-off frequency of less than 50 HZ.

33. The system of claim 30 wherein the filter means is a band pass filter in which the upper cut-off frequency is less than 50 HZ and the lower cut-off frequency is greater than 0.01 HZ.

34. The system of claim 22 wherein the processor means includes amplification means for amplifying the receive signal.

35. The system of claim 22 wherein the processor means includes digitizing means for digitizing said receive signal.

36. The system of claim 22 wherein the processor means is a microprocessor performing one or more of digitizing, amplifying and filtering tasks in software.

37. The system of claim 36 wherein the microprocessor is programmed with a neural network algorithm.

38. The system of claim 36 wherein the microprocessor is programmed with a neural network algorithm and is further programmed with a hidden Markov chain processor algorithm and/or a Kalman filter algorithm to enhance the signal to noise ratio of the receive signal input to the neural network.

39. The system of claim 22 further comprising display means for displaying the output signal.

40. A method of detecting insects in a structure including the steps of:
   transmitting a near field microwave signal into a part of the structure;
   receiving a receive signal that is amplitude modulated and/or phase shifted in relation to the transmitted near field microwave signal substantially by the insects crossing near field equal amplitude contours; and
   digitizing and analyzing the receive signal to provide an output signal indicative of the presence of the insects in the near field microwave signal.

41. The method of claim 40 further comprising adaptive recognition of termite indicative signals in a neural network.

42. The method of claim 41 wherein a hidden Markov chain processor algorithm and/or a Kalman filter algorithm are employed at an input to the neural network to enhance the signal to noise ratio of a signal input to the neural network.

43. A system for detecting insects in a structure, the system comprising:
   signal generator means operatively coupled to transmitter means to thereby transmit a near field microwave signal into a part of the structure;
   receiver means for receiving signals that are amplitude modulated and/or phase shifted in relation to the transmitted near field microwave signal substantially by the insects crossing near field equal amplitude contours and are indicative of the presence or otherwise of insects in a near field of the microwave signal; and
   processor means for digitizing and analyzing a receive signal to provide an output signal indicating the presence or otherwise of insects.

44. The system of claim 43 wherein the processor means is a microprocessor programmed with a neural network algorithm.

45. The system of claim 44 wherein the microprocessor is further programmed with a Markov chain processor algorithm and/or a Kalman filter algorithm to enhance the signal to noise ratio of the receive signal input to the neural network.

* * * * *